(12) United States Patent (10) Patent No.: US 7,479,752 B2
Messerly et al. (45) Date of Patent: Jan. 20, 2009

(54) ROTATION ACTUATOR FOR ENDOSCOPIC DEVICES

(75) Inventors: Jeffrey David Messerly, Cincinnati, OH (US); Gary W. Knight, West Chester, OH (US); Barry Thomas Jamison, Fairfield, OH (US); William D. Shaw, Jr., Cincinnati, OH (US)

(73) Assignee: Ethicon-Endo Surgery, Inc., Cincinnati, OH (US)

( * ) Notice: Subject to any disclaimer, the term of this patent is extended or adjusted under 35 U.S.C. 154(b) by 29 days.

(21) Appl. No.: 11/425,525

(22) Filed: Jun. 21, 2006

(65) Prior Publication Data

US 2007/0296365 A1 Dec. 27, 2007

(51) Int. Cl.
*G05B 19/04* (2006.01)

(52) U.S. Cl. .............................. 318/568.21; 318/568.12; 318/567

(58) Field of Classification Search ................. 318/567, 318/568.12, 568.14, 568.21; 606/46, 51, 606/205
See application file for complete search history.

(56) References Cited

U.S. PATENT DOCUMENTS 5,258,006 A * 11/1993 Rydell et al. ................ 606/205
5,478,351 A * 12/1995 Meade et al. ............... 606/205
5,603,723 A *  2/1997 Aranyi et al. ............... 606/205
6,110,171 A *  8/2000 Rydell ......................... 606/51
6,458,130 B1* 10/2002 Frazier et al. ................. 606/51
6,682,528 B2*  1/2004 Frazier et al. ................. 606/51
6,743,240 B2   6/2004 Smith et al.
2005/0277954 A1  12/2005 Smith et al.

* cited by examiner

*Primary Examiner*—Rina I Duda
(74) *Attorney, Agent, or Firm*—Nutter McClennen & Fish LLP

(57) ABSTRACT

Methods and devices are provided for rotating an end effector on a long, flexible medical device. The methods and devices utilize an actuator mechanism that is effective to rotate an end effector on the distal end of an elongate flexible shaft. The actuator mechanism is movable between a freely rotatable position and a rotationally resistant position. When the actuator mechanism is in a freely rotatable position, the actuator mechanism can be rotated to impart torque to the end effector, and thus at least a distal portion of the elongate shaft, to cause the end effector to rotate. In order to prevent the actuator mechanism from "freewheeling," wherein the actuator mechanism freely rotates in an opposite direction upon release rather than the end effector rotating in the desired direction, the actuator mechanism can be moved to the rotationally resistant position.

28 Claims, 12 Drawing Sheets

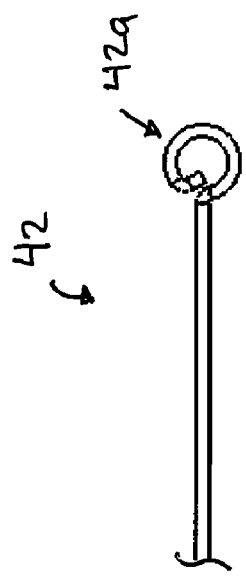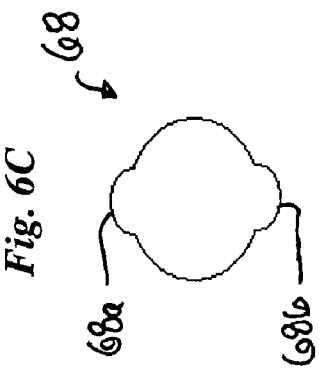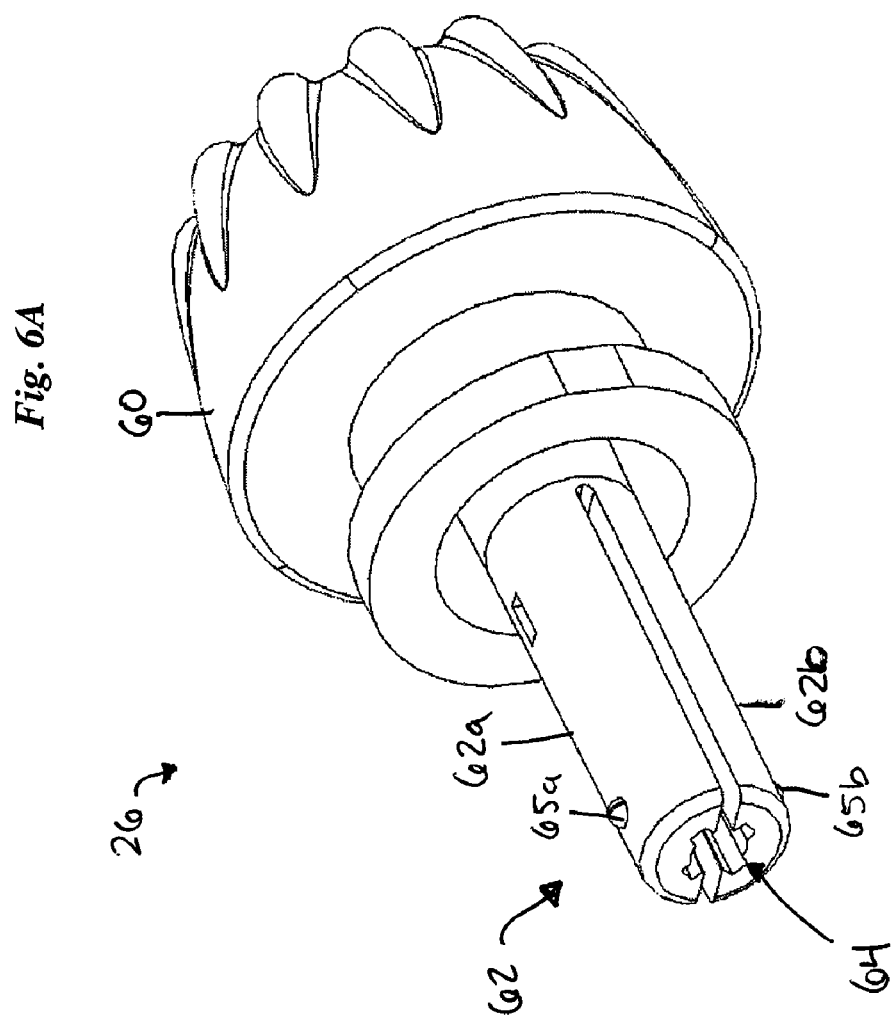

ROTATION ACTUATOR FOR ENDOSCOPIC DEVICES

FIELD OF THE INVENTION

The present invention relates to broadly to surgical devices, and in particular to methods and devices for rotating an end effector on a surgical device.

BACKGROUND OF THE INVENTION

Recently, many surgical devices have been made flexible for use in endoscopic procedures, allowing the devices to be inserted through a working channel of an endoscope. The ability to grasp tissue, apply fasteners, or perform various other procedures through an endoscope permits myriad minimally invasive surgical solutions to medical problems, especially those of the gastrointestinal tract.

Some endoscopic surgical devices include a flexible tubular shaft, a control member longitudinally movable relative to the tubular shaft, an end effector coupled to the distal ends of the tubular member and the control member, and a housing with controls for actuating the control member. Actuation of the control member relative to the tubular member causes operation of the end effector, which can be, for example, a pair of opposed tissue-effecting jaws. Some devices are also configured such that rotation of the control member can be effective to rotate the end effector.

One drawback of current endoscopic surgical devices resides in the difficulty to rotate the end effector. As mentioned above, rotation of a control member can rotate the end effector. This can be achieved by applying torque to the distal end of the tubular shaft to thereby rotate the shaft and thus rotate the end effector coupled thereto. For example, a knob coupled to the proximal end of the control member can be rotated to rotate the control member, and thereby rotate the tubular shaft and end effector. The knob is rotationally coupled to the control member and is allowed to freewheel; that is, the knob spins freely, providing minimal rotational resistance. Often, multiple turns of the knob are necessary to rotate the end effector a desired amount, as the rotation angle of the knob is greater than the corresponding rotation of the end effector because of the angular deformation of the control member due to its relatively long length and small diameter and also due to the torsional resistances provided by the shaft. When the user rotates the knob, the control member twists until the resistance torque is overcome, eventually causing the tubular shaft to rotate and thereby rotate the end effector. However, release of the knob between turns would allow the control member to un-twist, driving itself and the knob, as the knob is rotationally coupled to the control member and provides little rotational resistance, to a neutral energy state (state of zero or near zero angular deflection). As a result, the user must keep at least a finger on the knob to prevent the control member from unwinding as they impart successive rotations to the knob. This can be difficult to achieve comfortably and with only one hand, which is often necessary during surgical procedures.

Accordingly, there remains a need for improved methods and devices for rotating an end effector on an endoscopic surgical device.

SUMMARY OF THE INVENTION

The present invention provides various methods and devices for rotating an end effector on an endoscopic surgical device. In one embodiment, an endoscopic device is provided and includes a flexible elongate shaft having proximal and distal ends, an end effector coupled to the distal end of the elongate shaft, and a housing coupled to the proximal end of the elongate shaft. The housing can include an actuator mechanism associated with a distal end of the elongate shaft such that rotation of the actuator mechanism is effective to rotate the distal end of the elongate shaft and thereby rotate the end effector. The actuator mechanism can be movable between a freely rotatable position and a rotationally resistant position, in which the actuator mechanism is resistant to rotation.

While the actuator mechanism can have a variety of configurations, in one embodiment the actuator mechanism can be a rotatable knob. The rotatable knob can be rotatably disposed within an opening formed in the housing and it can be slidably movable relative to the housing along a longitudinal axis of the device. Sliding movement of the knob along the longitudinal axis can be effective to move the knob between the freely rotatable position and the rotationally resistant position. The housing can also include an engagement mechanism formed therein and configured to releasably engage a portion of the knob when the knob is in the rotationally resistant position. In one embodiment, the engagement mechanism can be a flange formed within the housing and configured to frictionally engage a portion of the knob when the knob is in the rotationally resistant position. In another embodiment, the engagement mechanism can be a flange formed within the housing and configured to engage detents formed on a portion of the knob when the knob is in the rotationally resistant position. In another aspect, the rotatable knob can include a deformable element and the housing can include an opening located therein and configured to receive and engage the deformable element to maintain the actuator mechanism in the rotationally resistant position.

The actuator mechanism can also have a variety of configurations, and in one embodiment the actuator mechanism can include a shaft having at least an end portion that is split into first and second halves. The housing can include an opening located therein and configured to receive and engage the first and second halves to maintain the actuator mechanism in the rotationally resistant position. In one exemplary embodiment, at least one of the first and second halves includes at least one surface feature formed thereon, and the opening includes at least one groove formed therein and configured to receive the at least one surface feature to appropriately resist rotation of the actuator mechanism.

In another embodiment, the actuator mechanism and the distal end of the elongate shaft can be associated by a flexible control wire extending through the elongate shaft between the actuator mechanism and the distal end of the elongate shaft. Rotation of the actuator member can be effective to torque the flexible control wire and thereby torque the elongate shaft to rotate the end effector.

The device can also include other features, such as a biasing element coupled to the actuator mechanism and adapted to bias the actuator mechanism to the freely rotatable position. In another embodiment, the housing can include a grasping mechanism movably coupled thereto, and movement of the grasping mechanism from a first position to a second position can be configured to move the actuator mechanism from the rotationally resistant position to the freely rotatable position. In other aspects, the end effector can include opposed jaws and movement of the grasping mechanism from the first position to the second position can be effective to close the opposed jaws.

In yet another embodiment, a surgical fastener applying device is provided and includes a flexible elongate shaft having proximal and distal ends, an end effector coupled to the distal end of the elongate shaft and including opposed jaws adapted to engage tissue therebetween and to apply at least one fastener to the engaged tissue, and a housing coupled to the proximal end of the elongate shaft and having an actuator mechanism rotatably coupled thereto. The actuator mechanism can be slidably movable between a first position, in which rotation of the actuator mechanism is effective to rotate a distal end of the elongate shaft to thereby rotate the end effector, and a second position, in which the actuator mechanism is resistant to rotation, i.e., rotationally resistant.

The housing can have a variety of configurations, but in one embodiment the housing can include an engagement mechanism formed therein and configured to releasably engage the actuator mechanism to maintain the actuator mechanism in the second position. The housing can also include a grasping mechanism movably coupled thereto and configured to move the actuator mechanism from the second position to the first position.

In yet another embodiment, a method for rotating an end effector on an endoscopic surgical device is provided and includes rotating an actuator mechanism on a housing of an endoscopic surgical device to rotate a distal end of an elongate shaft extending from the housing. The distal end of the elongate shaft can have an end effector coupled thereto that rotates therewith. The method can further include sliding the actuator mechanism along a longitudinal axis of the device to move the actuator mechanism to a rotationally resistant position, wherein the actuator mechanism, elongate shaft, and end effector are maintained in a rotated position. In an exemplary embodiment, the endoscopic surgical device is inserted through a body lumen.

In another embodiment, the distal end of the elongate shaft and actuator mechanism can be coupled by a flexible control wire, and rotating the actuator mechanism can torque the flexible control wire to cause the distal end of the elongate shaft and the end effector coupled thereto to rotate. The actuator can also be slid in an opposite direction along a longitudinal axis of the device to move the actuator mechanism to a freely rotatable position, in which any torque on the flexible control wire is released. The method can also include moving a grasping mechanism coupled to the housing to move the actuator mechanism from the rotationally resistant position to a freely rotatable position.

BRIEF DESCRIPTION OF THE DRAWINGS

The invention will be more fully understood from the following detailed description taken in conjunction with the accompanying drawings, in which:

FIG. 6A is a perspective view of a knob of the housing shown in FIG. 3;

FIG. 6B is a side view of a proximal portion of a flexible control wire for use with the knob of FIG. 6A;

FIG. 6C is a cross-sectional view of an opening formed in the housing shown in FIG. 3;

DETAILED DESCRIPTION OF THE INVENTION

Figure 1:
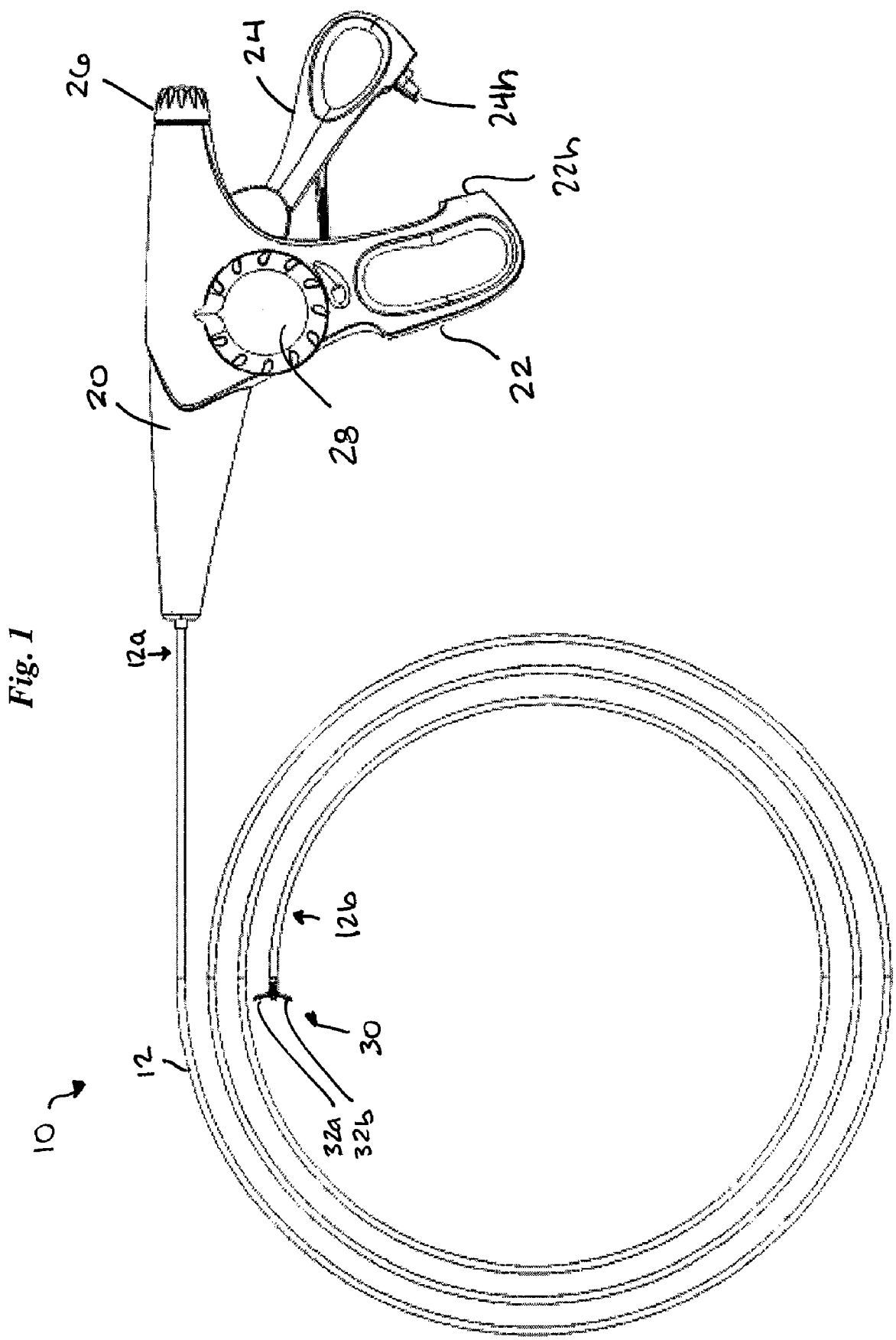
FIG. 1 is a side view of one exemplary embodiment of a surgical clip applier.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides methods and devices for rotating an end effector on a long, flexible medical device. The methods and devices utilize an actuator mechanism that is effective to rotate an end effector on the distal end of an elongate flexible shaft, and that is movable between a freely rotatable position and a rotationally resistant position. When the actuator mechanism is in a freely rotatable position, the actuator mechanism can be rotated to impart torque to a distal portion of the elongate shaft, thereby rotating the end effector. In order to maintain the actuator mechanism and thus the end effector in the rotated position, and to prevent the actuator mechanism from "freewheeling," wherein the actuator mechanism freely rotates in an opposite direction upon release rather than the end effector rotating in the desired direction, the actuator mechanism can be moved to the rotationally resistant position. The rotationally resistant position is a position in which the actuator mechanism is resistant to rotation such that free rotation or "freewheeling" is prevented, yet the resistance to rotation is preferably low enough to still allow a user to rotation the actuation mechanism (and, thereby, rotationally position the end effector). This is particularly advantageous with endoscopic devices which have a relatively long shaft through which the rotational forces must be transferred to rotate the end effector. Moreover, the rotationally resistant position is particularly useful where the actuator mechanism must be rotated several turns to position the end effector as desired. In such a situation, the engagement mechanism will prevent the actuator mechanism from "freewheeling" between turns in which the user needs to release and re-grasp the actuator mechanism.

A person skilled in the art will appreciate that, while the methods and devices are described in connection with an endoscopic clip applier, the concepts can be applied to a variety of other surgical, therapeutic, or diagnostic devices in which it is desirable to rotate an end effector. Moreover, the present invention has application in conventional endoscopic and open surgical instrumentation, as well application in robotic-assisted surgery. A person skilled in the art will also appreciate that, while the actuator mechanism is described as having a rotational resistant position, in other embodiments the rotationally resistant position can be one in which the actuator mechanism is locked and is prevented from rotating all together. The amount of resistant can be configured as may be necessary depending on the intended use.

FIG. 1 illustrates one exemplary embodiment of an endoscopic device having an actuator mechanism for controlling rotation of an end effector. While the actuator mechanism can be used with a variety of devices having end effectors for performing various procedures, such as fastening, manipulating, and treating tissue, FIG. 1 illustrates a flexible clip applier 10. As shown, the clip applier 10 generally includes a flexible elongate shaft 12 having a proximal end 12a coupled to a housing 20, and a distal end 12b with an end effector 30 coupled thereto. The end effector 30 includes opposed jaws 32a, 32b that are configured to engage tissue therebetween, and to apply a clip to the tissue.

The housing 20 can have a variety of configurations, but it preferably includes at least one handle to facilitate grasping of the device. Various handle assemblies known in the art can be used including, for example, spool style handles, syringe style handles, and various other handle configurations. In the illustrated embodiment, the housing 20 includes a pivoting trigger or lever style handle. In particular, the housing 20 is a generally pistol-shaped with a stationary handle 22 extending from a bottom surface thereof. A trigger 24 is pivotally coupled to the housing 20 and it is effective to pivot toward the stationary handle 22 to close opposed jaws 32a, 32b of the end effector. The housing 20 also includes a rotatable knob 26 which is effective to rotate the end effector 30, as well as a crank 28 which is effective to advance a clip through the shaft 12 and into the jaws 32a, 32b of the end effector 30. The three actuator mechanisms, i.e., the trigger 24, rotatable knob 26, and crank 28, will be discussed in more detail below.

The elongate shaft 12 that extends from the housing 20 can have a variety of configurations, but in an exemplary embodiment it is flexible or semi-flexible to allow the elongate shaft 12 to be introduced translumenally, e.g., through a natural orifice. While various materials and techniques can be used to form a flexible shaft, in the illustrated embodiment the elongate shaft 12 is formed form a friction reducing flexible outer sheath having a flat coil wire extending therethrough. The flexibility of the shaft 12 can vary along different portions of the shaft 12, and the shaft 12 can also be formed from one or more components that are mated together. In certain exemplary embodiments, as will be discussed in more detail below, the shaft 12 can include a flexible proximal portion and a distal portion that can be substantially rigid or that can have a similar or greater flexibility than the proximal portion. The distal portion can extend distally from a coupler, which will be discussed below, and it can connect to the end effector 30. In use, when the rotatable knob 26 is rotated to rotate the end effector 30, at least a distal region of the flexible proximal portion of the shaft 12 will twist to rotate the distal portion of the shaft 12, thereby rotating the end effector 30.

Figure 2:
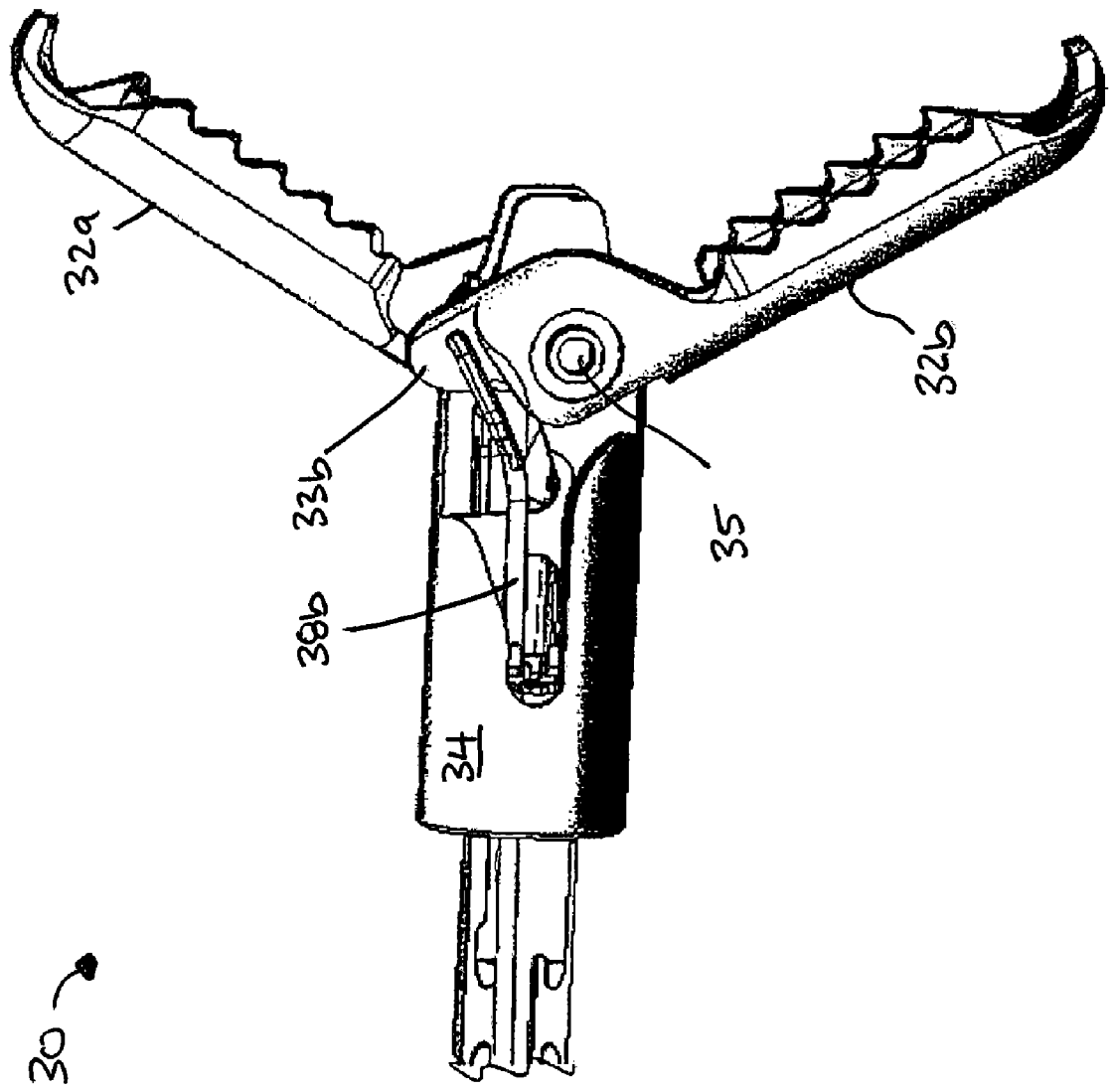
FIG. 2 is a side view of an end effector of the surgical clip applier of FIG. 1.

The end effector 30 coupled to the distal end 12b of the elongate shaft 12 can also have a variety of configurations, and one exemplary embodiment of an end effector 30 is shown in more detail in FIG. 2. As shown, the end effector 30 includes a jaw mount or clevis 34 that mates to the distal end 12b of the elongate shaft 12. First and second jaws 32a, 32b are pivotally mated to the clevis 34 via a mounting hole (only one mounting hole 35 is shown), and each jaw 32a, 32b includes a proximal tang (only one tang 33b is shown) that is coupled to a pull wire (only one pull wire 38b is shown) which extends through a distal portion of the elongate shaft 12 and mates to a coupler, as will be discussed in more detail below. Proximal axial movement of the pull wires is effective to close the opposed jaws 32a, 32b and thereby grasp tissue positioned therebetween, and distal movement of the pull wires is effective to open the opposed jaws 32a, 32b. The end effector 30 is also configured to apply a plurality of clips, sequentially, to tissue engaged between the jaws. This can be achieved using a clip advancing assembly, discussed in more detail below, which advances a clip into the jaws, and an anvil formed within each jaw 32a, 32b for deforming the clip.

Figure 3:
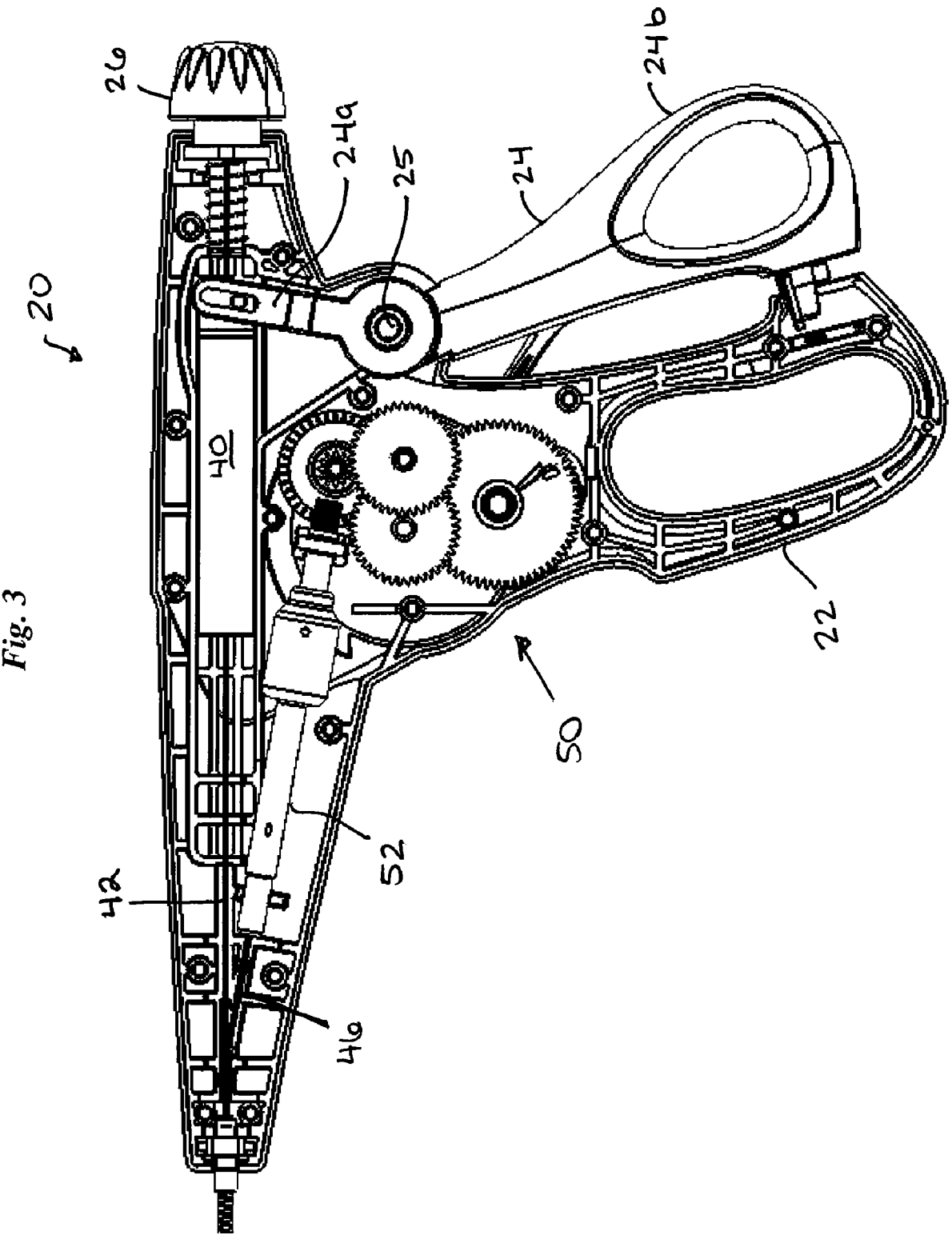
FIG. 3 is side view of a housing of the surgical clip applier of FIG. 1 with a portion of the housing removed to expose internal control components.
Figure 4:
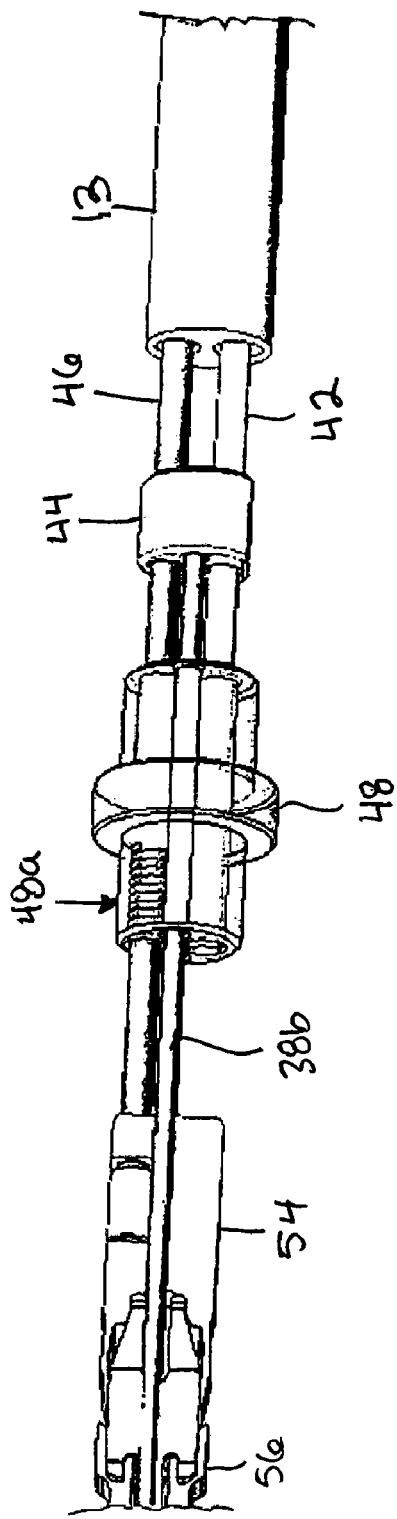
FIG. 4 is a partially transparent side view of a distal portion of a shaft of the device of FIG. 1, showing first and second control wires, a coupler, pull wires for moving the jaws, and a clip advancing mechanism.

As indicated above, the housing 20 includes three actuator mechanisms, a trigger 24 for opening and closing the jaws 32a, 32b, a rotatable knob 26 for rotating the end effector 30, and a crank 28 for advancing a clip into the jaws 32a, 32b. FIGS. 2, 3, and 4 illustrate the trigger 24 and jaw closing assembly, FIGS. 3 and 4 illustrate the rotatable knob 26 and end effector rotation assembly, and FIGS. 1, 3, 4, and 5 illustrate the crank 28 and clip advancing assembly. The assemblies and various exemplary configurations for each assembly are also described in more detail in commonly owned U.S. Publication No. 2005/0277954 filed on Jun. 14, 2004 and entitled "Endoscopic Clip Applier Actuator," which is hereby incorporated by reference in its entirety.

Turning first to FIG. 3, the trigger 24 is pivotally mounted within the housing 20 by a pivot pin 25, and includes a distal portion 24b having a thumb grip formed therein and a proximal extension arm 24a. The extension arm 24a is coupled to a shuttle assembly 40 which moves between proximal and distal positions within the housing 20. The shuttle assembly 40 can have various configurations and it can include various features, such as an overload mechanism. The particular configuration of the shuttle assembly 40 (or linkage) is described in more detail in US. Publication No. 2005/0277954. As shown in FIG. 3, the shuttle assembly 40 is coupled to a proximal portion of a first control wire 42, which extends through the elongate shaft 12. The distal end of the first control wire 42 mates to a joiner or coupler 44, which is shown in FIG. 4. The coupler 44 is positioned proximal to the end effector 30, i.e., the clevis 34 and jaws 32a, 32b. The coupler 44 is also positioned proximal to the distal portion of the elongate shaft. In particular, as previously discussed, the elongate shaft 12 can include a flexible proximal portion and a distal portion. The proximal and distal portions are mated by a rigid member 48. This can be done, for example, by laser welding both the proximal and distal portions to the rigid member 48, which is shown in FIG. 4. The coupler 44 is disposed within and mated to a distal region of the flexible proximal portion of the elongate shaft 12, just proximal to the rigid member 48. This allows the coupler 48 to apply a rotational torque to the distal region of the proximal portion of the elongate shaft 12, thereby twisting the elongate shaft 12 and thus rotating the distal portion of the elongate shaft 12 and the end effector 20 attached thereto. As further shown in FIG. 4, the device can also include an extruded plastic sheath 13 that runs through a majority of the length of the elongate shaft 12 (not shown in FIG. 4) to guide and protect the control wires 42, 46.

The coupler 44 can include four bores formed therethrough. One of the bores can fixedly mate to the distal end of the first control wire 42, as shown in FIG. 4. Another bore in the coupler 44 can receive a second control wire 46 used to advance a clip, as will be discussed below. The remaining two bores in the coupler 44 can fixedly mate to a proximal end of two pull wires (only one pull wire 38b is shown). As previously discussed with respect to FIG. 2, the distal ends of the pull wires mate to the tangs on the proximal end of each jaw 32a, 32b. As a result, when the trigger 24 is pivoted toward the stationary handle 22 to thereby pull the shuttle assembly 40 in a proximal direction, i.e., toward the back-end of the housing 20, the first control wire 42 is pulled proximally through the elongate shaft 12, thereby pulling the coupler 44 and the two pull wires attached thereto in a proximal direction. The opposed jaws 32a, 32b will thus move to a closed position to engage tissue therebetween. Conversely, when the trigger 24 is released, the pull wire 42 and coupler 44 can move distally to allow the jaws 32a, 32b to open.

Turning back to FIG. 3, the rotatable knob 26 for rotating the end effector 30 is also shown. In general, the knob 26 includes a lumen or bore formed therein that receives a proximal end of the first control wire 42. The lumen is shaped to allow free slidable movement of the first control wire 42 along its axis, and to rotationally couple the proximal end of the first control wire 42 to the knob, as will be discussed in more detail below. As a result, rotation of the knob 26 will rotate the control wire 42. The first control wire 42 is preferably formed from a semi-flexible material, such as a nickel-titanium alloy or stainless steel, which permits the first control wire 42 to transmit torque by rotation without taking a cast, and with minimal whipping. The first control wire 42 also preferably has a sufficiently large diameter to transmit force and torque, yet not so large that it is prevented from flexing as the elongate shaft 12 is passed through a tortuous lumen.

As previously discussed with respect to FIG. 4, the distal end of the first control wire 42 is mated to the coupler 44. Thus, when the knob 26 is rotated to rotate the first control wire 42, a torque is generated which causes rotation of the coupler 44, pull wires 38a (not shown) and 38b, and rigid member 48. The coupler 44 will thus rotate the distal region of the flexible proximal portion of the elongate shaft 12, thereby rotating the distal portion of the elongate shaft 12, and thereby rotating the end effector 30. As previously indicated, the rotatable knob 26 can also be configured to move between a rotationally resistant and a freely rotatable configuration. Various exemplary techniques for maintaining the knob 26 in the rotationally resistant position will be discussed in more detail below with respect to FIGS. 6A-7D.

Figure 5:
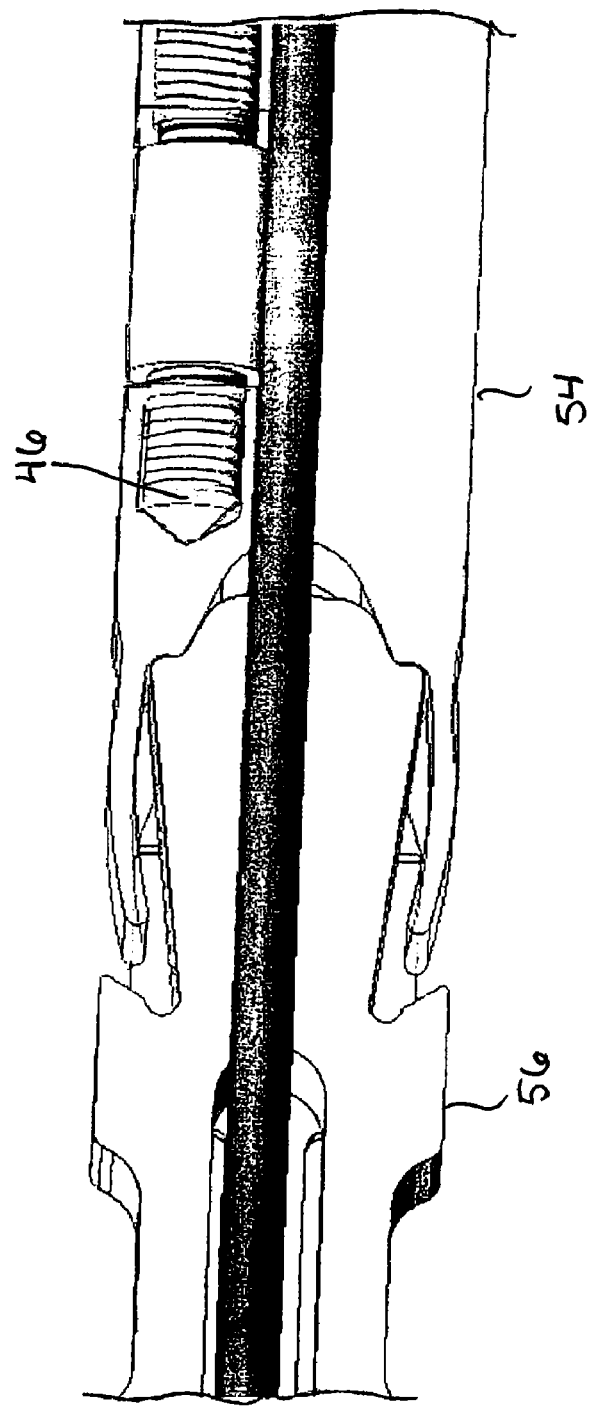
FIG. 5 is a perspective view of a distal portion of the clip advancing mechanism of FIG. 4.

FIG. 3 further illustrates a crank assembly 50 for advancing a clip stored in the distal portion of the elongate shaft 12. The crank assembly 50 is coupled to the crank 28, shown in FIG. 1, which is rotatably coupled to a sidewall of the housing 20. While not shown, a second crank can be disposed on the opposed side of the housing 20 to allow a user to selectively rotate either knob. Continuing to refer to FIG. 3, the crank assembly 50 includes a set of gears disposed within the housing 20 and configured to rotate in response to rotation of the crank 28. The gears communicate with one another to cause corresponding rotation of a transmission 52 that is mated to a proximal end of the second control wire 46. The second control wire 46 extends through the elongate shaft 12 and through a bore formed in the coupler 44, and it is threadably mated to a threaded bore 48a formed in the rigid member 48 (FIG. 4). The distal end of the second control wire 46 extends into a clip pusher 54, which is shown in FIG. 5 and which is described in more detail in US. Publication No. 2005/0277954. In general, rotation of the crank 28 is effective to rotate the second control wire 46. Since the second control wire 46 is threadably mated to the rigid member 48, which is fixed between the proximal and distal portions of the elongate shaft 12, the threaded bore 48a in the rigid member 48 will cause the second control wire 46 to move distally through the elongate shaft 12, thereby advancing the pusher 54 in a distal direction. The pusher 54 is positioned proximal to a series of clips 56 stored within a garage in the distal portion of the elongate shaft 12, and thus distal movement of the pusher 54 will advance the clips 56 through the shaft 12 to position a distal most clip within the jaws 32a, 32b of the end effector 30. A person skilled in the art will appreciate that a variety of other techniques can be used to advance a plurality of clips through the elongate shaft and to position a clip within the jaws.

As indicated above, the present invention provides various techniques for engaging an actuator mechanism, such as the rotatable knob 26, to maintain the end effector 30 at a fixed angular orientation and to prevent "freewheeling" of the knob 26. This position is referred to herein as the rotationally resistant position. This is particularly advantageous with endoscopic devices which have a relatively long shaft through which the rotational forces must be transferred to rotate the end effector. Moreover, the rotationally resistant position is particularly useful where the actuator mechanism must be rotated several turns to position the end effector as desired. In such a situation, the engagement mechanism will prevent the actuator mechanism from "freewheeling" between turns in which the user needs to release and re-grasp the actuator mechanism because the resistance to rotation in the rotationally resistant position is greater than the return torque provided by the angular deflections of the rotation system during use. In an exemplary embodiment, the rotationally resistant position can provide a minimum resistive torque to resist rotation, yet it can have a maximum torque limit that allows for user positioning (i.e., rotation) in the rotationally resistant position within ergonomic capabilities,. By way of non-limiting example, the minimum resistive torque in the rotationally resistant position can be about 0.8 inch-ounces (0.5 inch-pounds) and the maximum torque that allows ergonomic manipulation can be about 5.0 inch-pounds, as applied to an actuation mechanism and control wire of a practical size and materials.

While various techniques can be used to engage the actuator mechanism, in an exemplary embodiment the rotatable knob 26 is slidably movable along a longitudinal axis of the device 10 between a rotationally resistant position, in which a portion of the rotatable knob 26 is engaged by a portion of the housing 20 or a component disposed within the housing 20, and a freely rotatable position in which the knob 26 is free to rotate. Various techniques can be used to engage the knob 26 and maintain the knob 26 in the rotationally resistant position, including an interference fit, a threaded connection, a snap-lock connection, and other mating techniques known in the art.

As shown in FIG. 6A, knob 26 includes a proximal grasping member 60 configured to be grasped by a user, and shaft 62 extending distally from the grasping member 60. The shaft 62 is configured to extend through an opening formed in the back end of the housing 20 and, as previously explained, it includes a lumen 64 extending therethrough for slidably receiving the proximal end of the first control wire 42. As shown in FIG. 6A, the lumen 64 can be keyed to allow free slidable movement of the first control wire 42, yet to couple rotation of the first control wire 42 to the rotatable knob 26. The proximal end 42a of the first control wire 42 is shown in FIG. 6B, and as shown the proximal end 42a is bent into a shepherd's crook to allow the keyed lumen 64 in the knob 26 to engage the first control wire 42. As further shown in FIG. 6A, the shaft 62 of the knob 26 is split longitudinally such that the shaft 62 includes first and second halves 62a, 62b that are deflectable relative to one another. The shaft 62 can also optionally include one or more surface features formed thereon and configured to help resist rotation of the knob 26, as will be discussed below. In the illustrated embodiment, the first and second halves 62a, 62b each include a protrusion 65a, 65b formed thereon. A person skilled in the art will appreciate that the surface features can have a variety of other configurations, such a grooves, teeth, ridges, etc., and that various other techniques instead of surface features can optionally be used.

Figure 6D:
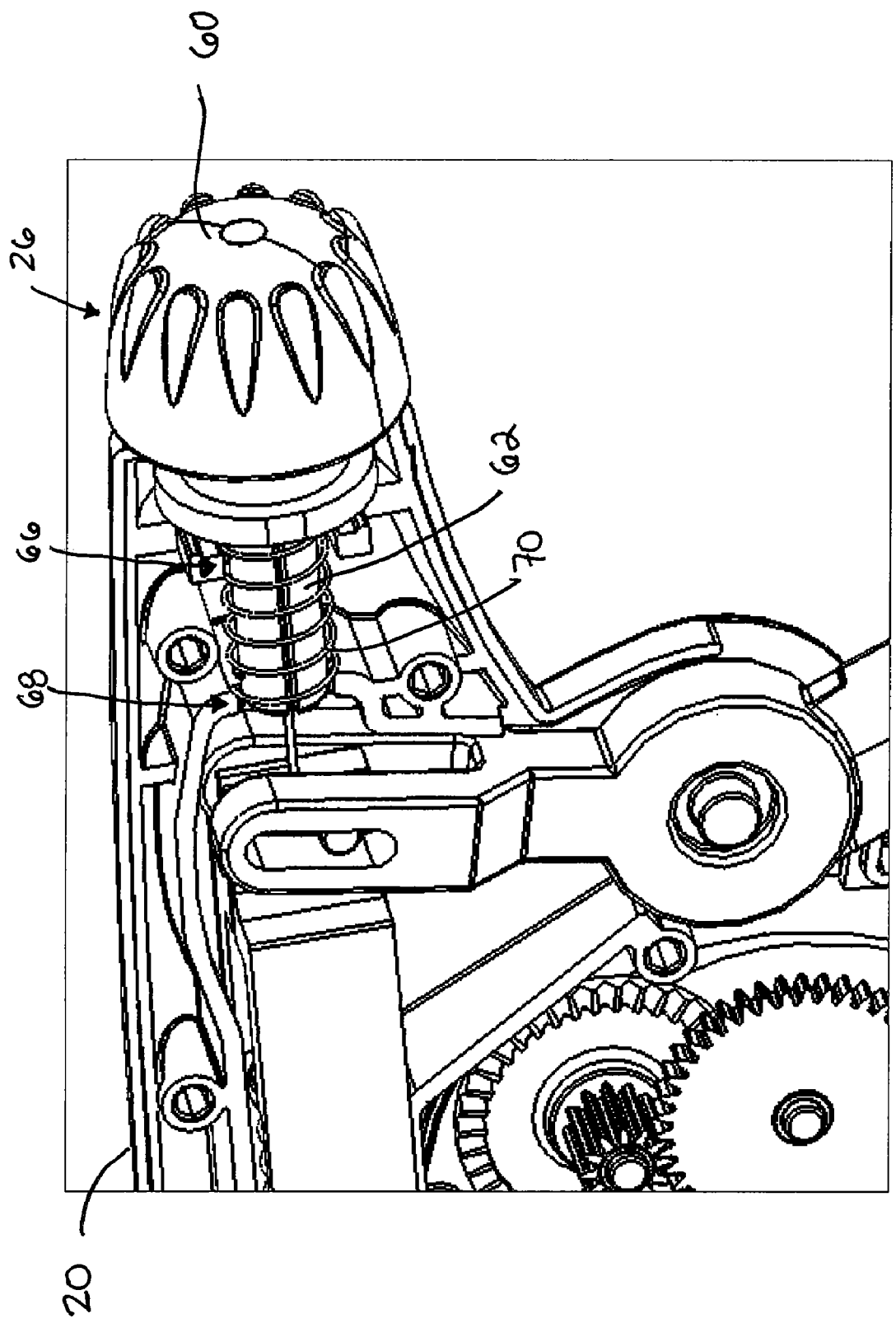
FIG. 6D is a side perspective view of a portion of the housing of FIG. 3, with a portion of the housing removed to show the knob of FIG. 6A disposed therein.

In use, the split shaft 62 and the protrusions 65a, 65b allow the housing 20 to engage and resist rotation of the knob 26. In particular, the interior portion of the housing 20 can be molded or otherwise shaped to have walls formed therein that define one or more openings for receiving the shaft 62 of the knob 26 therethrough. As shown in FIG. 6D, the interior walls define a first opening 66 that receives a proximal portion of the shaft 62, and a second opening 68 that receives the distal end of the shaft 62. The first opening 66 can function to merely align the shaft 62 and allow free slidable movement thereof along the axis of the shaft 62. The second opening 68, on the other hand, can be sized to engage the shaft 62 when the shaft 62 is positioned therein, thereby engaging and preventing free wheeling of the knob 26.

Figure 6E:
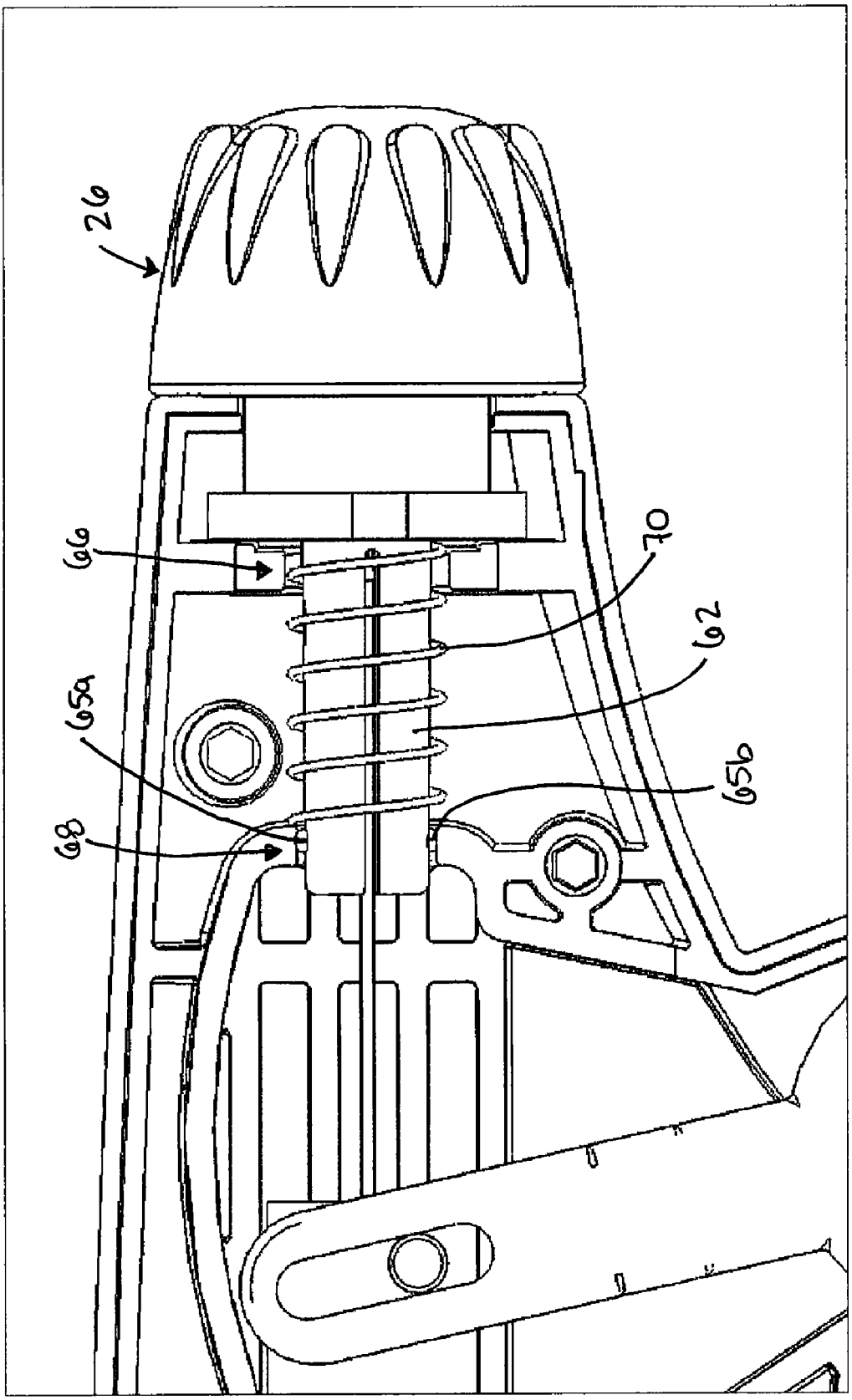
FIG. 6E is a side view of the portion of the housing shown in FIG. 6D, with the knob moved to a rotationally resistant position.

The knob 26 can be moved to the rotationally resistant position by sliding the knob 26 from a proximal position, shown in FIG. 6D, to a distal position to position the distal end of the shaft 62 within the second opening 68, a shown in FIG. 6E. The split configuration of the shaft 62 will allow the halves 62a, 62b of the shaft 62 to be compressed toward one another to allow the second opening 68 to engage the shaft 62. The protrusions 65a, 65b can be received within corresponding grooves or cut-outs formed in the second opening 68 to allow the second opening 68 to resist rotation of the shaft 62. A cross-sectional view of the second opening 68 is shown in FIG. 6C, which illustrates opposed cut-outs or grooves 68a, 68b formed in the second opening 68 for seating the protrusions 65a, 65b. While only a single pair of grooves, 68a and 68b are shown, the knob 26 can include multiple pairs of grooves around the circumference of opening 68 to give a finer resolution of resistive positions.

Figure 6F:
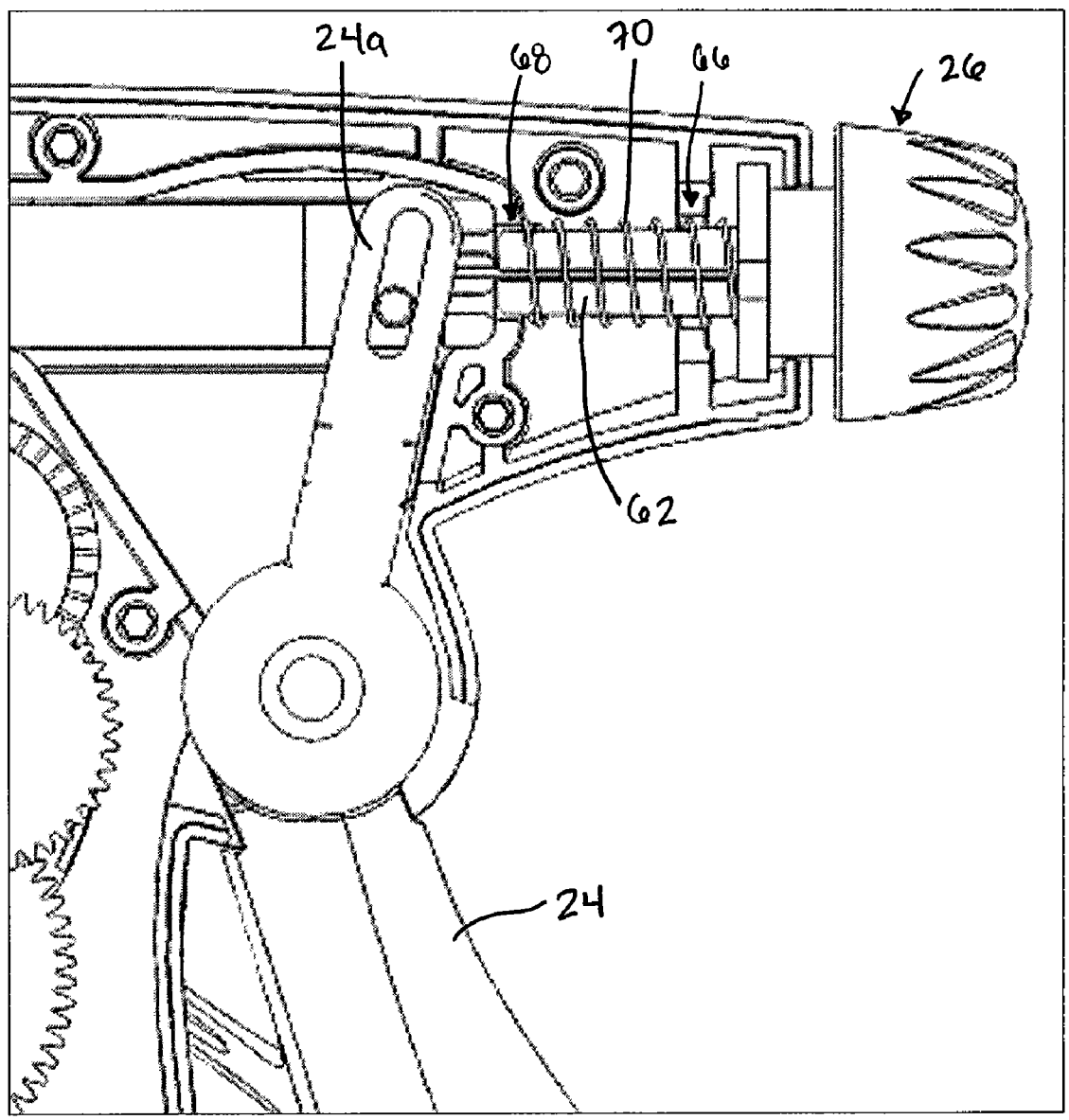
FIG. 6F is a side view of the portion of the housing shown in FIG. 6E, with a trigger pivoted to release the knob from the rotationally resistant position.

When desired, the knob 26 can be moved to the freely rotatable position, shown in FIG. 6D, by pulling the knob 26 in a proximal direction to remove the distal end of the shaft 62 from the second opening 68. Alternatively, the trigger 24 can be pivoted toward the stationary member 22 to release the knob 26 from the rotationally resistant position. As shown in FIG. 6F, the proximal portion 24a of the trigger 24 will abut against the distal end of the shaft 62, thereby forcing the shaft 62 in a proximal direction, and thus moving the knob 26 proximally to the freely rotatable position. As shown in FIGS. 6D-6F, a compression spring 70 can optionally be disposed around the shaft 62 of the knob 26 to bias the knob 26 toward the proximal, freely rotatable position. The compression spring 70 will also help return the knob 26 to the freely rotatable position when the trigger 24 is actuated to release the knob 26.

A person skilled in the art will appreciate that various other techniques can be used to allow the second opening 68 to engage the proximal end of the shaft 62 on the knob 26. For example, the shaft 62 and opening 68 can include a ratchet mechanism, or teeth and protrusions, that allow the opening 68 to engage and prevent rotation of the shaft 62. Such a configuration is particularly advantageous as it could be configured to allow the user the rotate the knob 26 to a desired degree, e.g., dial the knob to a particular position with a positional resolution being defined by the number and spacing of the detents. In other embodiments, other regions of the housing 20 can be configured to engage the shaft 62 or other portions of the knob 26. For example, the first opening 66 can engage the shaft 62, or alternatively the opening in the proximal-most or back end of the housing 20 can be configured to engage the proximal grasping member 60 of the knob 26.

Figure 7A:
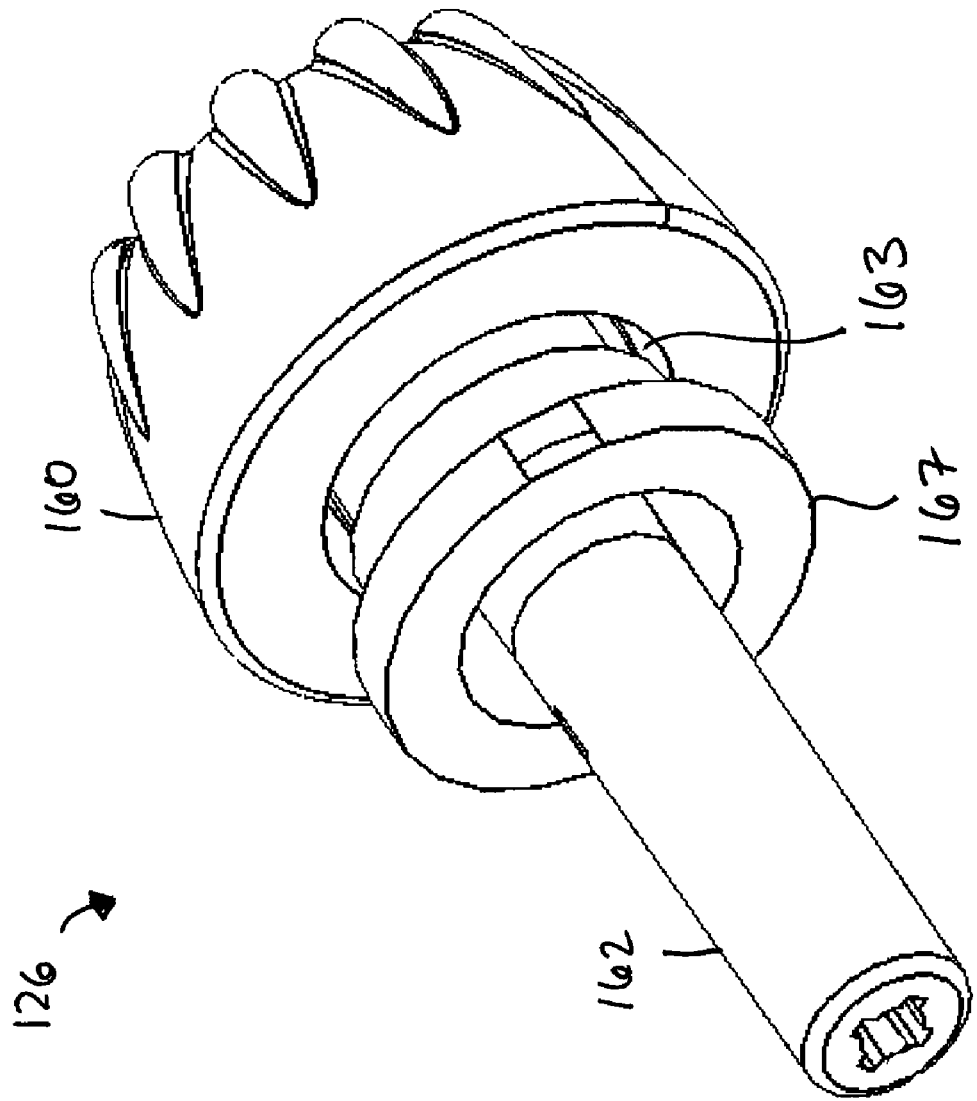
FIG. 7A is a perspective view of another embodiment of a knob for use with the housing of the device shown in FIG. 3.
Figure 7B:
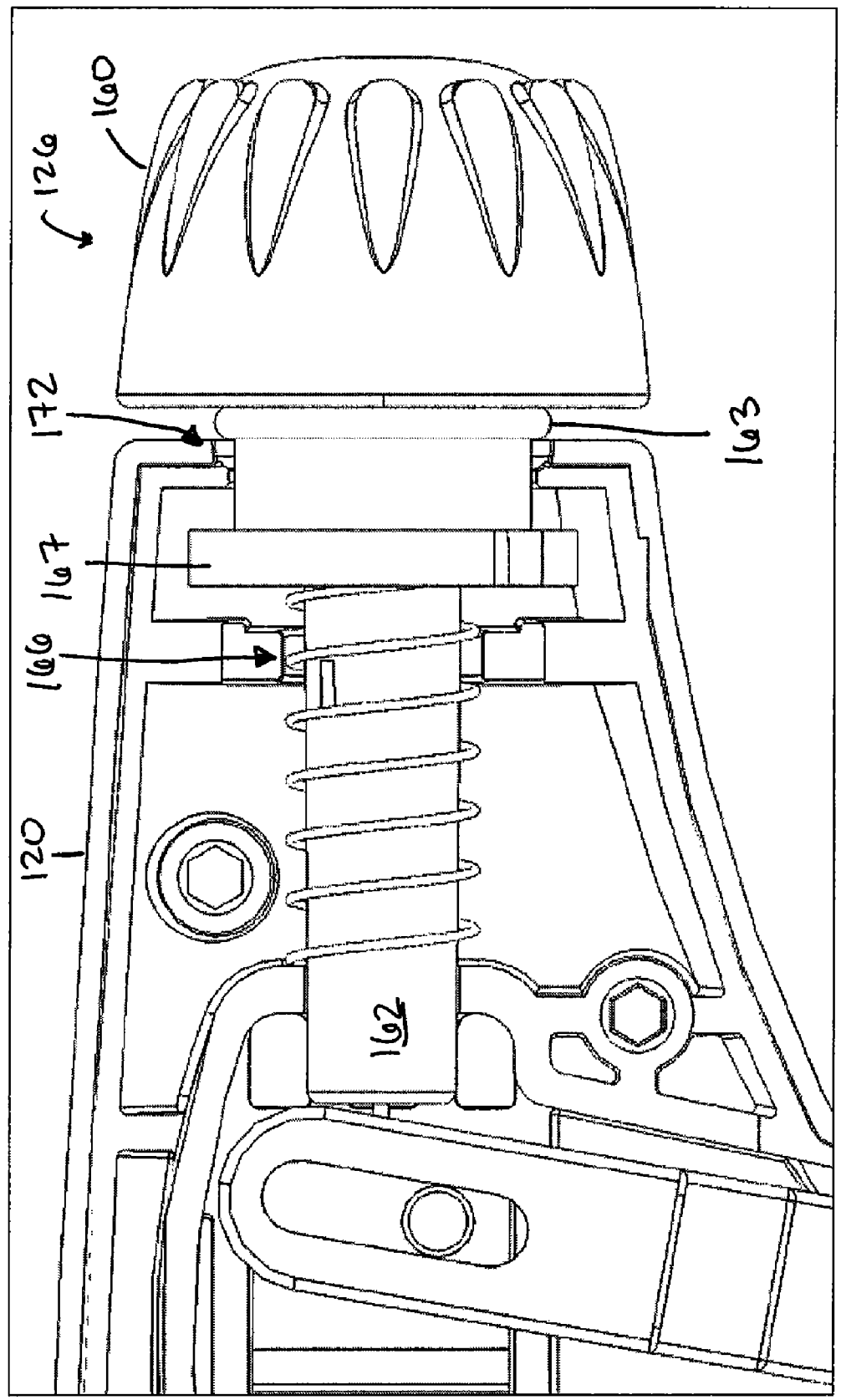
FIG. 7B is a side view of a portion of a housing having a portion of the housing removed to show the knob of FIG. 7A disposed therein.
Figure 7C:
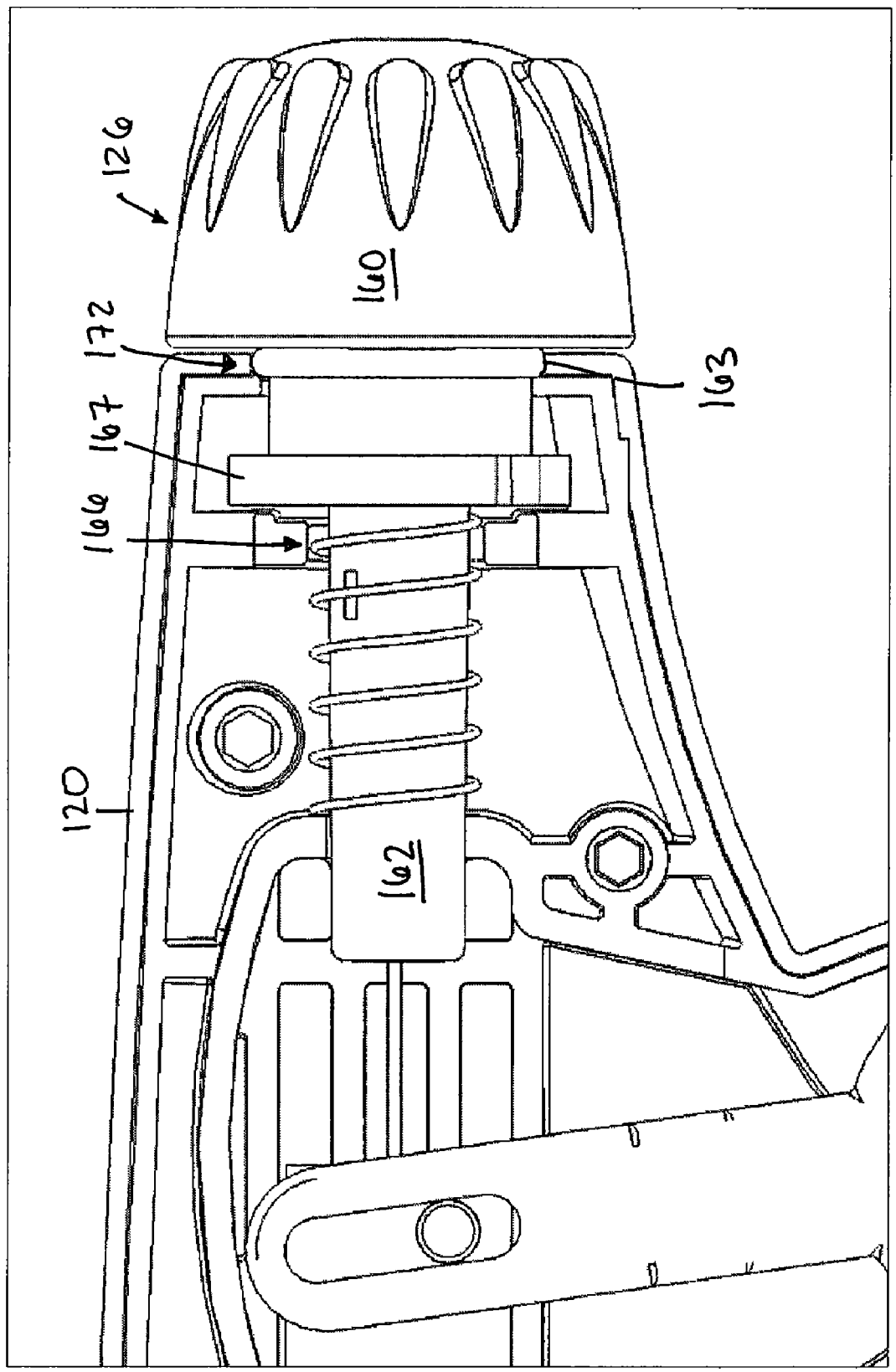
FIG. 7C is a side view of the portion of the housing shown in FIG. 7B, with the knob moved to a rotationally resistant position.
Figure 7D:
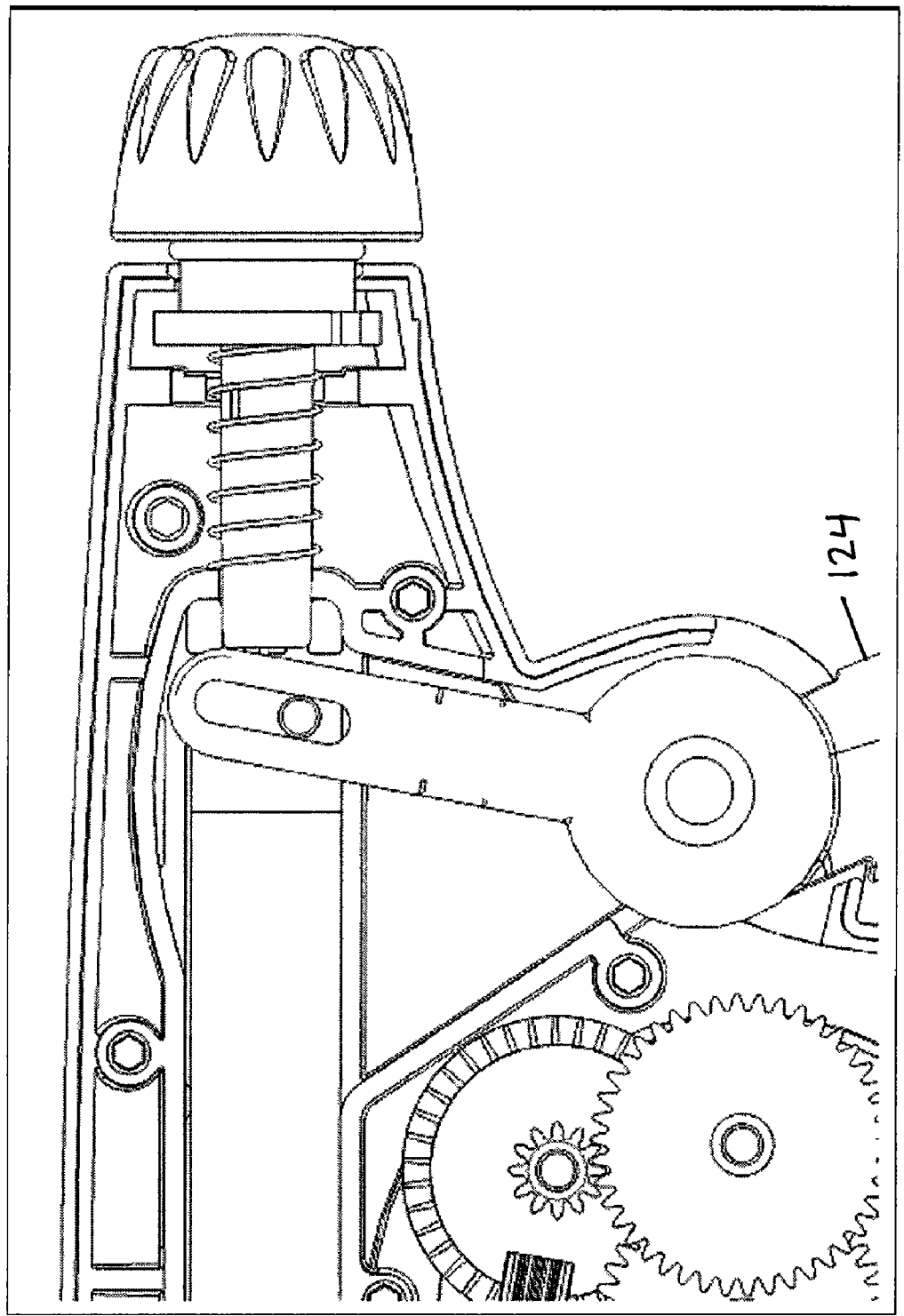
FIG. 7D is a side view of the portion of the housing shown in FIG. 7C, with a trigger pivoted to release the knob from the rotationally resistant position.

FIGS. 7A-7C illustrate one embodiment of a knob 126 having a proximal grasping portion 160 that is configured to be engaged by an opening 172 formed in the back of the housing 120. While the knob 126 is shown as a separate embodiment from the knob 26 described with respect to FIGS. 6A-6, the features of each knob 26, 126 can be used in combination with one another to provide a more secure rotationally resistant configuration. In this embodiment, rather than configuring the distal end of the shaft to be engaged by an opening defined by walls formed within the housing, the proximal grasping member 160, or a proximal end of the shaft 162, can be configured to be engaged by an opening 172 formed in the back end of the housing 120. In particular, as shown in FIG. 7A, an enlarged diameter region or a flange 163 can be formed around the proximal-most end of the shaft 162, and thus adjacent to the grasping member 160. The opening 172 in the back side of the housing 120 can be sized to engage the enlarged diameter region or flange 163 to prevent rotation of the knob 126. Thus, in use, the knob 126 can be moved between a proximal, freely rotatable position shown in FIG. 7B, in which the enlarged diameter region or flange 163 is positioned distal of the opening 172 in the housing 120, and a distal, rotationally resistant position shown in FIG. 7C, in which the enlarged diameter region or flange 163 is positioned within and engaged by the opening 172 in the housing 120. As further shown in FIGS. 7A-7C, the knob 126 can also include a second flange 167 formed distal of the enlarged diameter region or flange 163, and configured to be positioned between the opening 172 in the housing 120 and the first opening 166 formed by the walls within the housing 120. The second flange 167 will prevent the knob 126 from being removed from the housing 120 in use. While not shown, the enlarged diameter region or flange 163 and/or the opening 172 in the housing 120 can also include surface features, such as those previously described, to further prevent rotation of the knob 126 relative to the housing 120 when the knob 126 is in the rotationally resistant position. As yet another alternative, the enlarged diameter region or flange 163 can be replaced by an O-ring or similar deformable element that is formed on, mated to, or resides in a groove in the knob 126 at the location of the enlarged diameter region or flange. The knob 126 can also be released from the rotationally resistant position by pulling the knob 126 proximally or by actuating the trigger 124, as previously described and as shown in FIG. 7D.

In use, the various devices disclosed herein can be inserted translumenally, i.e., through a natural orifice, or through another access port. Referring to the device of FIG. 1, for example, the shaft 12 can be delivered through an endoscope or other endoscopic delivery device. The trigger 24 is preferably actuated to move the jaws 32a, 32b to the closed position for insertion. As shown in FIG. 1, the trigger 24 and stationary member 22 can each include a hook 24h, 22h formed thereon for locking the trigger 24 in the actuated position. Once the jaws 32a, 32b are positioned at the desired location, the trigger 24 can be released to open the jaws 32a, 32b. The jaws 32a, 32b can be positioned through movement of the coil shaft 12 and by rotating the knob 26 to position tissue to be clipped between the jaws 32a, 32b. As previously explained, rotation of the knob 26 will torque the first control member 42, thereby rotating the coupling member 44 (FIG. 4), and thus the distal region of the flexible proximal portion of the shaft 12. As a result, the distal portion of the shaft 12 and the end effector 30 will rotate. In order to maintain the knob 26 in the rotated position, either during successive turns of the knob 26 or once the knob 26 is rotated to a desired degree, the knob 26 can be moved distally to the rotationally resistant position, in which the knob 26 is resistant to rotation and the end effector 30 is maintained at a desired angular orientation. The trigger 24 can then be actuated again, i.e., moved toward the stationary member 22, to close the jaws 32a, 32b and engage tissue therebetween. As the trigger 24 is actuated, it will force the knob 26 into the freely rotatable position, thereby allowing free rotation of the knob 26 and releasing any torque applied to the first control wire 42. The crank 28 is then turned to advance a clip into the jaws 32a, 32b, which can function as an anvil to deform the clip. The trigger 24 can then be released once again to release the clip and tissue from the jaws 32a, 32b, and the device 10 can be removed.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning and/or replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. It is preferred that the device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An endoscopic device, comprising:
a flexible elongate shaft having proximal and distal ends;
an end effector coupled to the distal end of the elongate shaft; and
a housing coupled to the proximal end of the elongate shaft, the housing including an actuator mechanism associated with a distal end of the elongate shaft such that rotation of the actuator mechanism is effective to rotate the distal end of the elongate shaft and thereby rotate the end effector, the actuator mechanism being movable between a freely rotatable position and a rotationally resistant position in which the actuator mechanism is resistant to rotation.

2. The device of claim 1, wherein the actuator mechanism comprises a rotatable knob.

3. The device of claim 2, wherein the rotatable knob is rotatably disposed within an opening formed in the housing and is slidably movable relative to the housing along a longitudinal axis of the device.

4. The device of claim 3, wherein sliding movement of the knob along the longitudinal axis is effective to move the knob between the freely rotatable position and the rotationally resistant position.

5. The device of claim 4, wherein the housing includes an engagement mechanism formed therein and configured to releasably engage a portion of the knob when the knob is in the rotationally resistant position.

6. The device of claim 5, wherein the engagement mechanism comprises a flange formed within the housing and configured to frictionally engage a portion of the knob when the knob is in the rotationally resistant position.

7. The device of claim 5, wherein the engagement mechanism comprises a flange formed within the housing and configured to engage detents formed on a portion of the knob when the knob is in the rotationally resistant position.

8. The device of claim 1, wherein the actuator mechanism includes a shaft having at least an end portion that is split into first and second halves, and wherein the housing includes an opening located therein and configured to receive and engage the first and second halves to maintain the actuator mechanism in the rotationally resistant position.

9. The device of claim 8, wherein at least one of the first and second halves includes at least one surface feature formed thereon, and wherein the opening includes at least one groove formed therein and configured to receive the at least one surface feature to prevent rotation of the actuator mechanism.

10. The device of claim 2, wherein the rotatable knob includes a deformable element and wherein the housing includes an opening located therein and configured to receive and engage the deformable element to maintain the actuator mechanism in the rotationally resistant position.

11. The device of claim 1, wherein, when the actuator mechanism is in the rotationally resistant position, a resistance to rotation provided by the housing to the actuator mechanism is between about 0.5 and 5.0 inch pounds.

12. The device of claim 1, wherein, when the actuator mechanism is in the rotationally resistant position, a resistance to rotation provided by the housing to the rotation mechanism is about 1.2 inch pounds.

13. The device of claim 1, further comprising a biasing element coupled to the actuator mechanism and adapted to bias the actuator mechanism to the freely rotatable position.

14. The device of claim 1, wherein the actuator mechanism and the distal end of the elongate shaft are associated by a flexible control wire extending through the elongate shaft between the actuator mechanism and the distal end of the elongate shaft.

15. The device of claim 14, wherein rotation of the actuator member is effective to torque the flexible control wire and thereby torque the distal end of the elongate shaft to rotate the end effector.

16. The device of claim 1, wherein the housing includes a grasping mechanism movably coupled thereto, and wherein movement of the grasping mechanism from a first position to a second position is configured to move the actuator mechanism from the rotationally resistant position to the freely rotatable position.

17. The device of claim 16, wherein the end effector includes opposed jaws and wherein movement of the grasping mechanism from the first position to the second position is effective to close the opposed jaws.

18. A surgical fastener applying device, comprising:
   a flexible elongate shaft having proximal and distal ends;
   an end effector coupled to the distal end of the elongate shaft and including opposed jaws adapted to engage tissue therebetween and to apply at least one fastener to the engaged tissue; and
   a housing coupled to the proximal end of the elongate shaft and having an actuator mechanism rotatably coupled thereto, the actuator mechanism being slidably movable between a first position, in which rotation of the actuator mechanism is effective to rotate a distal end of the elongate shaft to thereby rotate the end effector, and a second position, in which the actuator mechanism is resistant to rotation.

19. The device of claim 18, wherein the housing includes an engagement mechanism formed therein and configured to releasably engage the actuator mechanism to maintain the actuator mechanism in the second position.

20. The device of claim 18, further comprising a grasping mechanism movably coupled to the housing and configured to move the actuator mechanism from the second position to the first position.

21. A method for rotating an end effector on an endoscopic surgical device, comprising:
   rotating an actuator mechanism on a housing of an endoscopic surgical device to rotate a distal end of an elongate shaft extending from the housing, the distal end of the elongate shaft having an end effector coupled thereto that rotates therewith; and
   sliding the actuator mechanism along a longitudinal axis of the device to move the actuator mechanism to a rotationally resistant position, wherein the actuator mechanism, elongate shaft, and end effector are maintain in a rotationally resistant position.

22. The method of claim 21, wherein the distal end of the elongate shaft and actuator mechanism are coupled by a flexible control wire, and wherein rotating the actuator mechanism torques the flexible control wire to cause the distal end of the elongate shaft and the end effector coupled thereto to rotate.

23. The method of claim 22, further comprising sliding the actuator mechanism in an opposite direction along a longitudinal axis of the device to move the actuator mechanism to a freely rotatable position in which any torque on the flexible control wire is released.

24. The method of claim 21, further comprising moving a grasping mechanism coupled to the housing, the grasping mechanism moving the actuator mechanism from the rotationally resistant position to a freely rotatable position.

25. The method of claim 21, wherein a resistive torque applied to the actuator mechanism in the rotationally resistant position is between about 0.5 and 5.0 inch pounds.

26. The method of claim 21, wherein a resistive torque applied to the actuator mechanism in the rotationally resistant position is about 1.2 inch pounds.

27. The method of claim 21, wherein the endoscopic surgical device is inserted through a body lumen.

28. The method of claim 21, further including the step of sterilizing the endoscopic surgical device after at least one use.

* * * * *